US007850669B1

(12) United States Patent
Moore et al.

(10) Patent No.: US 7,850,669 B1

(45) Date of Patent: Dec. 14, 2010

(54) FEEDING APPARATUS

(76) Inventors: Betty C. Moore, 4601 Emerson Ave., Parkersburg, WV (US) 26104; Byron J. Moore, 4601 Emerson Ave., Parkersburg, WV (US) 26104

( * ) Notice: Subject to any disclaimer, the term of this patent is extended or adjusted under 35 U.S.C. 154(b) by 745 days.

(21) Appl. No.: 11/480,240

(22) Filed: Jul. 3, 2006

(51) Int. Cl.
*A61F 5/44* (2006.01)

(52) U.S. Cl. .................. 604/343; 604/179; 128/207.17

(58) Field of Classification Search ................ 604/174, 604/179, 343; 128/202.27, 912, 207.17, 128/DIG. 1
See application file for complete search history.

(56) References Cited

U.S. PATENT DOCUMENTS 1,911,229 A * 5/1933 Gleim ........................ 604/174
3,161,199 A * 12/1964 Sands ......................... 604/179
4,437,463 A * 3/1984 Ackerman ............. 128/207.17
4,668,225 A * 5/1987 Russo et al. ................ 604/270
4,795,442 A * 1/1989 Traflet ........................ 604/179
4,915,104 A * 4/1990 Marcy ................... 128/207.18
4,944,732 A 7/1990 Russo
5,048,512 A 9/1991 Turner et al.
5,117,818 A * 6/1992 Palfy ..................... 128/204.11
5,304,145 A 4/1994 Blair
5,549,657 A 8/1996 Stern et al.
D393,310 S 4/1998 Russo
6,280,422 B1 8/2001 Sanchez-Browning
D503,467 S 3/2005 Flashinski et al.
7,004,170 B1 * 2/2006 Gillstrom ............... 128/207.18

* cited by examiner

*Primary Examiner*—Kevin C Sirmons
*Assistant Examiner*—Deanna K Hall

(57) ABSTRACT

A feeding apparatus includes a feeding tube that has a first end and a second end. A tether is removably attached to the feeding tube and is configured to secure the feeding tube to a neck or torso of a person receiving the feeding tube.

6 Claims, 3 Drawing Sheets

FEEDING APPARATUS

BACKGROUND OF THE INVENTION

1. Field of the Invention

The present invention relates to feeding tube devices and more particularly pertains to a new feeding tube device for supplying nutrients directly to a person's stomach without fear that the device will become dislodged or leak.

2. Description of the Prior Art

The use of feeding tube devices is known in the prior art. While these devices fulfill their respective, particular objectives and requirements, these devices typically rely on adhesive tape to secure the feeding tube in place. However, the adhesive may irritate a person's skin and looses its effectiveness over a period of time. This can cause leaks and accidental removal of the feeding tube. For this reason, the need remains for a device that secures a feeding tube to a person in such a manner that does not rely on adhesives and that can be easily adjusted for different sized patients.

SUMMARY OF THE INVENTION

The present invention meets the needs presented above by generally comprising a feeding tube that has a first end and a second end. A tether is removably attached to the feeding tube and is configured to secure the feeding tube to a neck of a person receiving the feeding tube.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
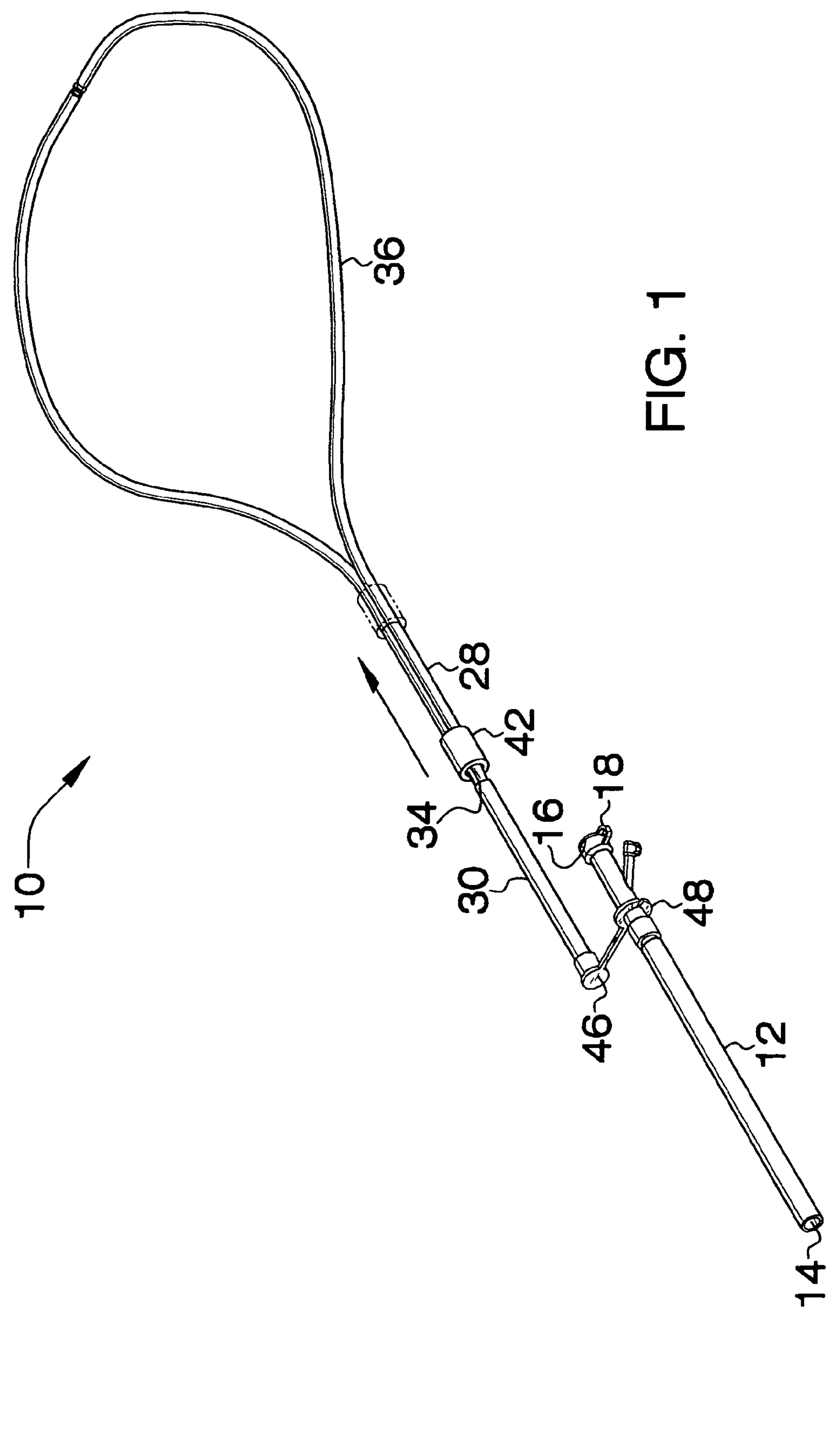
FIG. 1 is a perspective view of a feeding apparatus according to the present invention.
Figure 2:
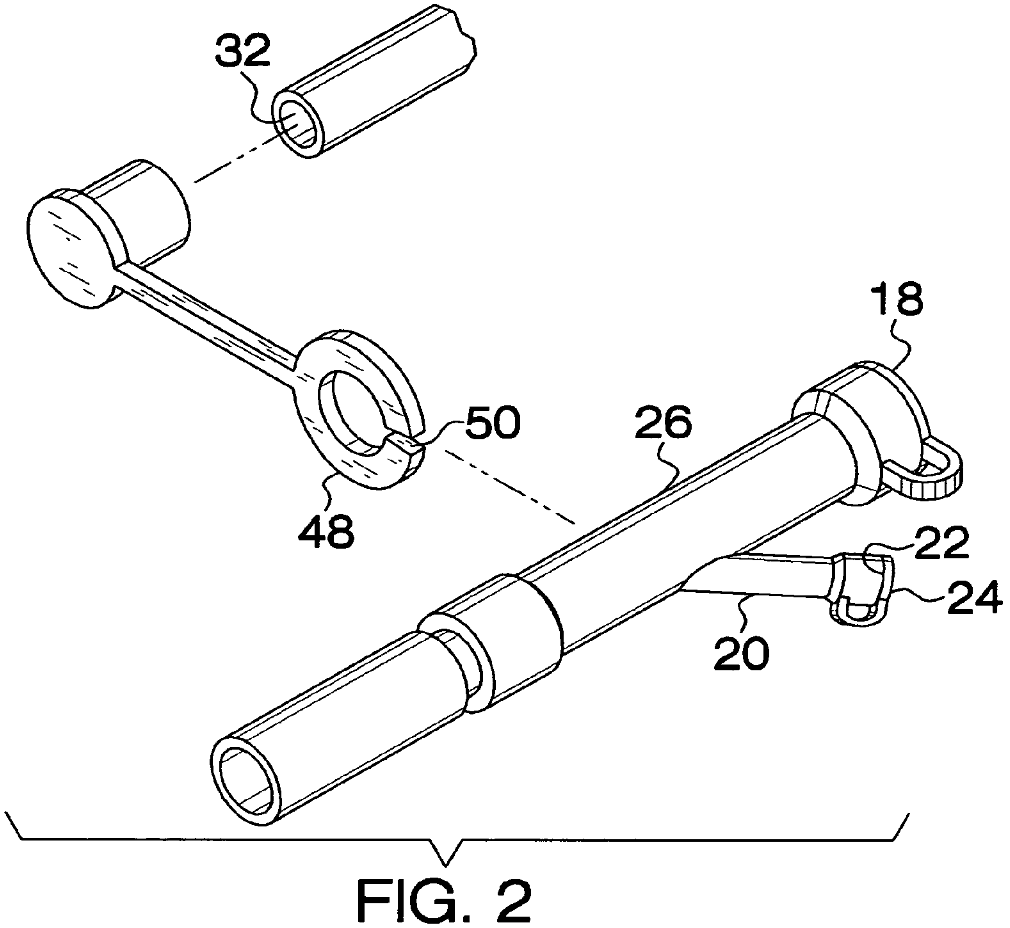
FIG. 2 is a perspective view of the present invention.
Figure 3:
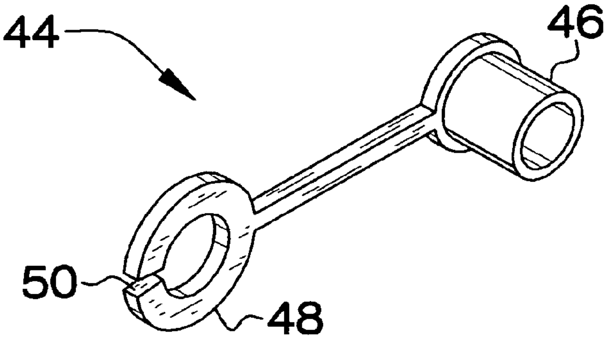
FIG. 3 is a perspective view of a connector of the present invention.
Figure 4:
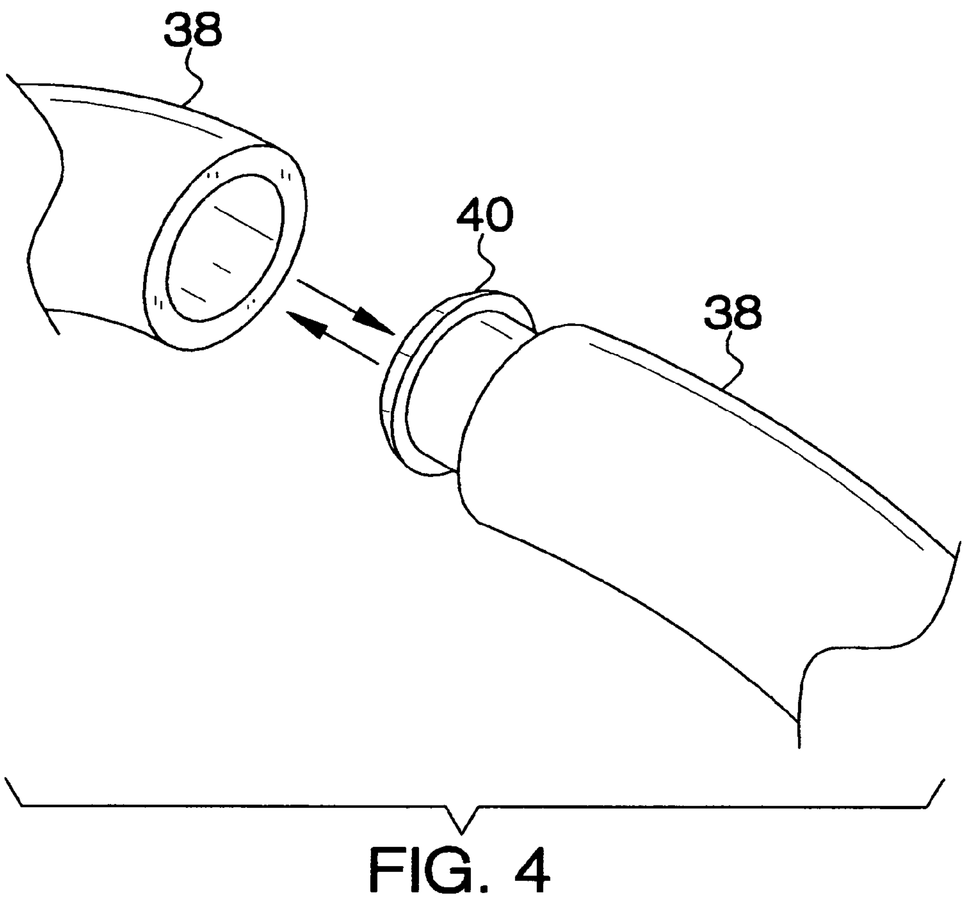
FIG. 4 is a perspective view of a portion of a loop of the present invention.

With reference now to the drawings, and in particular to FIGS. 1 through 4 thereof, a new feeding tube device embodying the principles and concepts of the present invention and generally designated by the reference numeral 10 will be described.

As best illustrated in FIGS. 1 through 4, the feeding apparatus 10 generally comprises a feeding tube 12 that has a first end 14 and a second end 16. A cap 18 is removably positioned over and closes the second end 16 of the feeding tube 12. The first end 14 of the feeding tube 12 is to be inserted into a stomach of a patient. A secondary conduit 20 is fluidly coupled to the feeding tube 12. The secondary conduit 20 has an open distal end 22 with respect to the feeding tube 12. The secondary conduit 20 is positioned adjacent to the second end 16 of the feeding tube 12. A cover 24 is removably positioned over and closes the distal end 22. The secondary conduit 20 allows for the receiving supplements and the like. The secondary conduit 20 may be part of an adapter portion 26 of the feeding tube 12 which may be removed for attachment to different lengths of tubing.

A tether 28 is removably attached to the feeding tube 12 and is configured to secure the feeding tube 12 to a neck of a person receiving the feeding tube 12. The tether 28 includes an elongated member 30 that has a first end 32 and a second end 34. A loop 36 is attached to and extends away from the second end 34 of the elongated member 30. The loop 36 is extendable around the neck of the person. The loop 36 may include two separable sections 38 joinable with a connecting member 40 so that one or both of the separable sections 38 may be slid under the neck of the patient and then joined together. A slide 42 is mounted on the elongated member 30. The slide 42 is extendable over the second end 34 of the elongated member 30 and onto the loop 36 to selectively decrease a circumference of the loop 36.

A connector 44 releasably couples the tether 36 to the feeding tube 12. The connector 44 includes a female coupler 46 releasably receiving the first end 32 of the elongated member 30. A ring 48 is attached to the female coupler 46. The ring 48 is configured for receiving and frictionally engaging the feeding tube 12. The ring 48 has a break 50 therein for releasing the ring from the feeding tube 12.

In use, the tether 28 is extended around the neck of a person and the first end 14 of the feeding tube 12 then inserted into the stomach through the lower chest area of the person. The tether 28 prevents movement of the feeding tube 12, which can cause leaks, and prevent it from being accidentally removed from the stomach. If the tether 28 is of sufficient length, it may also be extended around the torso or chest of the person should the person's neck be injured or other medical equipment prevents the tether 28 from being positioned around the person's neck.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A stomach feeding and tethering combination comprising:

a feeding tube having a first end and a second end;

a tether being removably attached to said feeding tube and being configured to secure said feeding tube to a neck or torso of a person receiving said feeding tube, said tether including an elongated member having a first end and a second end, a loop being attached to and extending away from said second end of said elongated member, said loop being extendable around the neck or torso of the person, said tether extending away from said loop to only allow said loop to extend around any portion of the neck or torso, said first end of said tether being spaced from said loop; and a slide being mounted on said elongated member, said slide being extendable over said second end of said elongated member and onto said loop to selectively decrease a circumference of said loop.

2. The combination according to claim 1, further including a cap being removably positioned over and closing said second end of said feeding tube.

3. The combination according to claim 1, further including a secondary conduit being fluidly coupled to said feeding tube, said secondary conduit having an open distal end with respect to said feeding tube, said secondary conduit being positioned adjacent to said second end of said feeding tube, a cover being removably positioned over and closing said distal end.

4. The combination according to claim 1, further including a connector releasably coupling said tether to said feeding tube, said connector including a female coupler releasably receiving said first end of said elongated member, a ring being attached to said female coupler, said ring being configured for receiving and frictionally engaging said feeding tube, said ring and said female coupler being attached to each other by an arm, said arm spacing said ring and said female coupler from each other.

5. The combination according to claim 4, wherein said ring has a break therein for releasing said ring from said feeding tube.

6. A stomach feeding and tethering combination comprising:

a feeding tube having a first end and a second end, a cap being removably positioned over and closing said second end of said feeding tube;

a secondary conduit being fluidly coupled to said feeding tube, said secondary conduit having an open distal end with respect to said feeding tube, said secondary conduit being positioned adjacent to said second end of said feeding tube, a cover being removably positioned over and closing said distal end;

a tether being removably attached to said feeding tube and being configured to secure said feeding tube to a neck or torso of a person receiving said feeding tube, said tether including an elongated member having a first end and a second end, a loop being attached to and extending away from said second end of said elongated member, said loop being extendable around the neck or torso of the person, said tether extending away from said loop to only allow said loop to extend around any portion of the neck or torso, said first end of said tether being spaced from said loop;

a connector releasably coupling said tether to said feeding tube, said connector including a female coupler releasably receiving said first end of said elongated member, a ring being attached to said female coupler, said ring being configured for receiving and frictionally engaging said feeding tube, said ring having a break therein for releasing said ring from said feeding tube, said ring and said female coupler being attached to each other by an arm, said arm spacing said ring and said female coupler from each other; and a slide being mounted on said elongated member, said slide being extendable over said second end of said elongated member and onto said loop to selectively decrease a circumference of said loop.

* * * * *